(12) United States Patent
Patil et al.

(10) Patent No.: US 12,344,829 B2
(45) Date of Patent: Jul. 1, 2025

(54) BIOREACTOR TRAY

(71) Applicant: GLOBAL LIFE SCIENCES SOLUTIONS USA LLC, Marlborough, MA (US)

(72) Inventors: Haresh Digambar Patil, Bangalore (IN); Anoop Bhargav, Bangalore (IN); Praveen Paul, Bangalore (IN); Sebastian John, Bangalore (IN)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 1115 days.

(21) Appl. No.: 16/345,492

(22) PCT Filed: Oct. 26, 2017

(86) PCT No.: PCT/EP2017/077387
§ 371 (c)(1),
(2) Date: Apr. 26, 2019

(87) PCT Pub. No.: WO2018/077994
PCT Pub. Date: May 3, 2018

(65) Prior Publication Data
US 2019/0309251 A1 Oct. 10, 2019

(30) Foreign Application Priority Data
Oct. 28, 2016 (IN) .............................. 201611037086

(51) Int. Cl.
*C12M 1/00* (2006.01)
*B01F 31/23* (2022.01)
(Continued)

(52) U.S. Cl.
CPC ............. *C12M 27/16* (2013.01); *B01F 31/23* (2022.01); *B01F 35/2215* (2022.01);
(Continued)

(58) Field of Classification Search
CPC . C12M 1/12; C12M 3/06; C12M 1/00; C12M 1/02; C12M 1/34; C12M 1/38; B01J 19/28
See application file for complete search history.

(56) References Cited

U.S. PATENT DOCUMENTS 5,156,082 A * 10/1992 Fukuda .............. G05D 23/1951
99/403
10,731,122 B2   8/2020 Hata et al.
(Continued)

FOREIGN PATENT DOCUMENTS

FR          2519020 A1      7/1983
JP      2011152077 A        8/2011
(Continued)

OTHER PUBLICATIONS

JP-H07284444-A original and machine translation. Document date Oct. 31, 1995. (Year: 1995).*

(Continued)

*Primary Examiner* — Lydia Edwards
(74) *Attorney, Agent, or Firm* — CM Law; Jeff B. Vockrodt (57) ABSTRACT

A tray configured to be provided on a base station of a bioreactor system, said tray comprising a bottom and surrounding side walls and being configured to hold a bioreactor bag, said bottom comprising at least two bottom parts, whereof one is a middle part of the bottom, wherein at least one of the bottom parts is movable into at least a first and a second position, wherein said first position provides the bottom parts substantially flush with each other providing a substantially plane bottom of the tray and said second position provides a bottom of the tray having a recessed middle part.

14 Claims, 7 Drawing Sheets

(51) Int. Cl.
*B01F 35/221* (2022.01)
*B01F 35/513* (2022.01)
*B01F 35/92* (2022.01)
*C12M 1/12* (2006.01)
*C12M 1/34* (2006.01)
*C12M 3/06* (2006.01)
*B01F 35/90* (2022.01)

(52) U.S. Cl.
CPC ............ *B01F 35/513* (2022.01); *B01F 35/92* (2022.01); *C12M 23/04* (2013.01); *B01F 2035/99* (2022.01); *C12M 23/14* (2013.01)

(56) References Cited

U.S. PATENT DOCUMENTS

| | | | |
|---|---|---|---|
| 2005/0186669 | A1 | 8/2005 | Ho et al. |
| 2010/0129899 | A1* | 5/2010 | Oosterhuis .............. B01F 31/23 |
| | | | 435/287.1 |
| 2010/0144022 | A1* | 6/2010 | Surapaneni ............ C12M 23/48 |
| | | | 435/289.1 |
| 2012/0100576 | A1 | 4/2012 | Goletz et al. |
| 2012/0231504 | A1* | 9/2012 | Niazi ..................... C12M 25/14 |
| | | | 435/69.51 |
| 2012/0258441 | A1 | 10/2012 | Gebauer et al. |
| 2016/0152938 | A1* | 6/2016 | Akerstrom ............ C12M 41/12 |
| | | | 374/120 |
| 2017/0313967 | A1* | 11/2017 | Andersson ............. C12M 23/50 |

FOREIGN PATENT DOCUMENTS

| | | |
|---|---|---|
| JP | 2013514804 A | 5/2013 |
| WO | 2012000502 A1 | 1/2012 |
| WO | 2013137813 A1 | 9/2013 |
| WO | 2016062833 A1 | 4/2016 |
| WO | 2016121292 A1 | 8/2016 |

OTHER PUBLICATIONS

Office Action received in India Application No. 201611037086 dated Feb. 11, 2022, with partial translation, 5 pages.

Office Action received in Japanese Application No. 2019-522664 dated Aug. 2, 2021, with translation, 6 pages.

* cited by examiner

BIOREACTOR TRAY

CROSS-REFERENCE TO RELATED APPLICATIONS

This application is a filing under 35 U.S.C. 371 of international application number PCT/EP2017/077387, filed Oct. 26, 2017, which claims priority to application No. 201611037086 filed in India on Oct. 28, 2016, the entire disclosures of each of which are hereby incorporated by reference.

TECHNICAL FIELD OF THE INVENTION

The present invention relates to a tray configured to be provided on a base station of a bioreactor system, a bioreactor system and a method for culturing cells in a bioreactor system.

BACKGROUND OF THE INVENTION

Bioreactors are used for culturing cells. One type of bioreactor is a rocking bioreactor which will agitate the cell culture within the bioreactor bag by providing a rocking motion to the bag. This is also referred to as a wave motion. In cell therapy cells are retrieved from a patient or a donor and then prepared and grown in different steps before they are provided to a patient as cell therapy. Incubators are often used for growing low volumes of cell cultures and in a later stage of the cell culturing where the volumes are larger bioreactors, such as a rocking bioreactor can be used. Transferring of the cells from incubators to rocking bioreactors is both a risk for loss of cells and a risk for contamination of the cells. Furthermore incubators need a lot of space in cleanrooms which is expensive.

SUMMARY

It is an object of the present invention to provide an improved bioreactor system and method for culturing cells.

It is also an object of the present invention to provide a method for culturing cells and a bioreactor system in which risk for contamination and loss of cells is decreased.

It is also an object of the present invention to provide a more effective and safe method and system for culturing cells.

The above objectives are addressed by a tray, a bioreactor system and a method for culturing cells as described in the independent patent claims.

Hereby a rocking bioreactor can be used also for early cell expansion, i.e. cell cultures with low volume. And furthermore the same bioreactor can be used for both small culture volumes and larger culture volumes. In prior art bioreactors there are often problems if low volume cell cultures are provided in a too large rocking bioreactor. These problems are related to that cells can be destroyed by the rocking motion when there is too little culture and cells could be lost due to condensation. With this invention the size of the tray can be adapted for different volumes of cell culture provided in the bioreactor bag and hereby the same bioreactor bag can be used for first early cell expansion which is usually performed in incubators and then also for later cell expansion. Hereby the cell culture need not be transferred from incubator to bioreactor and risk of cell loss and contamination is decreased. Furthermore cleanroom space is saved.

In one aspect of the invention a tray is provided, which tray is configured to be provided on a base station of a bioreactor system, said tray comprising a bottom and surrounding side walls and being configured to hold a bioreactor bag, said bottom comprising at least two bottom parts, whereof one is a middle part of the bottom, wherein at least one of the bottom parts is movable into at least a first and a second position, wherein said first position provides the bottom parts substantially flush with each other providing a substantially plane bottom of the tray and said second position provides a bottom of the tray having a recessed middle part.

In one aspect of the invention a bioreactor system comprising a base station and a tray as described above is provided.

In a further aspect of the invention a method for culturing cells in a bioreactor system is provided, wherein said method comprising the steps of:

determining a volume or weight of a cell culture provided in a bioreactor bag which is positioned in a tray in the bioreactor system;

positioning at least one bottom part of a bottom of said tray comprising at least two bottom parts into one of at least a first position and a second position in dependence of said determined volume or weight, said first position providing the bottom parts substantially flush with each other providing a substantially plane bottom of the tray and said second position providing a bottom of the tray having a recessed middle part.

In one embodiment of the invention the tray is configured to be provided on a base station of a rocking bioreactor system.

In one embodiment of the invention the bottom comprises a first part being the middle part and a second part surrounding said first part.

In one embodiment of the invention said first part is movable into the first and the second positions.

In one embodiment of the invention the bottom parts each comprises at least one heater. Hereby one or more of the bottom parts can be heated separately in dependence of the position of the middle part of the bottom and/or in dependence of a volume or weight of the content in the bioreactor bag.

In one embodiment of the invention the middle part comprises a temperature sensor. Hereby the heaters can be controlled in dependence of a sensed temperature in the bioreactor bag.

In one embodiment of the invention the tray further comprises a positioning device by which at least one of the bottom parts can be provided in the at least two different positions.

In one embodiment of the invention said base station comprises a control device connected to at least one heater in each bottom part of the tray and to the positioning device of the tray, wherein said control device is arranged to control the heaters in the tray in dependence of the position of the at least one bottom part which is moved into at least two different positions by the positioning device.

In one embodiment of the invention said base station comprises a weight measuring device configured for measuring the weight of a bioreactor bag provided in the tray and said base station further comprises a control device which is connected to at least one heater in each bottom part of the tray and to the weight measuring device, wherein said control device is arranged to control the heaters in dependence of a weight of the bioreactor bag measured in the weight measuring device.

In one embodiment of the invention the control device further is connected to the positioning device and arranged to control the positioning device to provide at least one of the bottom parts of the tray in either the first position or the second position in dependence of the measured weight.

In one embodiment of the invention the control device is further connected to a temperature sensor provided in the middle part of the bottom of the tray and wherein the control system is arranged to control the heaters in the tray in dependence of the sensed temperature.

In one embodiment of the invention the method further comprises the step of:
  controlling one or more heaters provided in the tray in dependence of the position of the at least one bottom part which is positioned into at least two different positions or in dependence of a measured weight of the bioreactor bag.

In one embodiment of the invention the method further comprises the step of measuring a temperature in the bioreactor bag and controlling the heaters in the tray in dependence of said measured temperature.

DETAILED DESCRIPTION OF EMBODIMENTS

The present invention relates to a bioreactor system and to a tray in said rocking bioreactor system. It also relates to a method for culturing cells in a bioreactor system. The bioreactor system can be a rocking bioreactor system, but also other types of bioreactor systems where a tray is used to hold the bioreactor bag, such as for example shaken reactors, should be covered by this patent application.

Figure 1A:
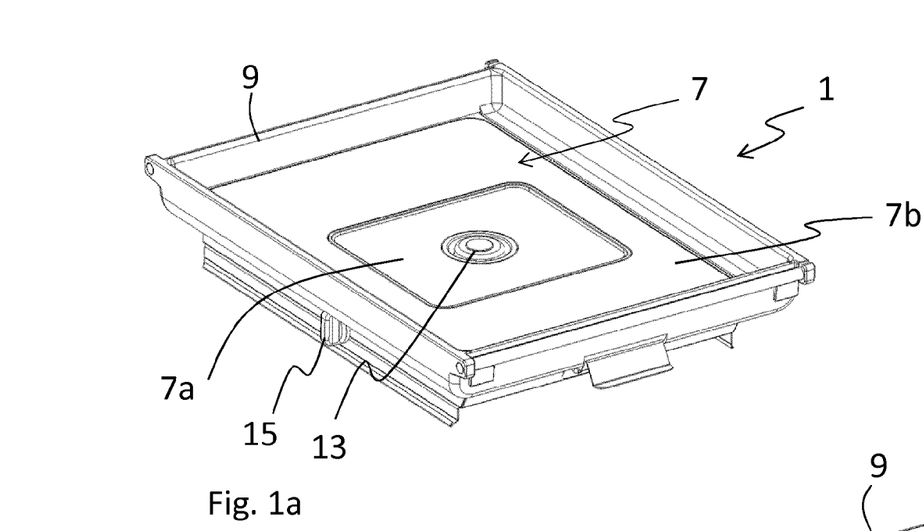
FIG. 1a shows schematically a tray according to one embodiment of the invention with a first part of the tray bottom provided in a first position.
Figure 1B:
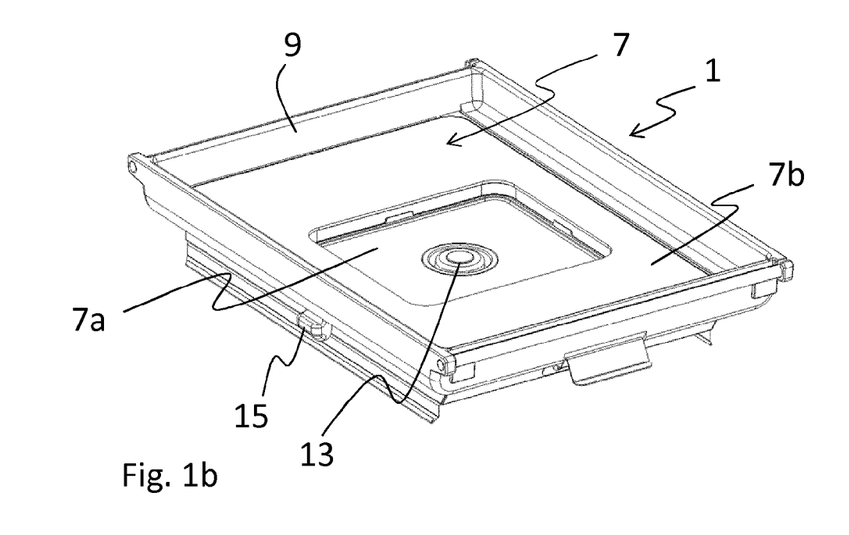
FIG. 1b shows schematically the same tray as shown in FIG. 1a with the first part of the tray bottom provided in a second position.

FIGS. 1a and 1b show schematically a tray according to one embodiment of the invention.

Figure 2A:
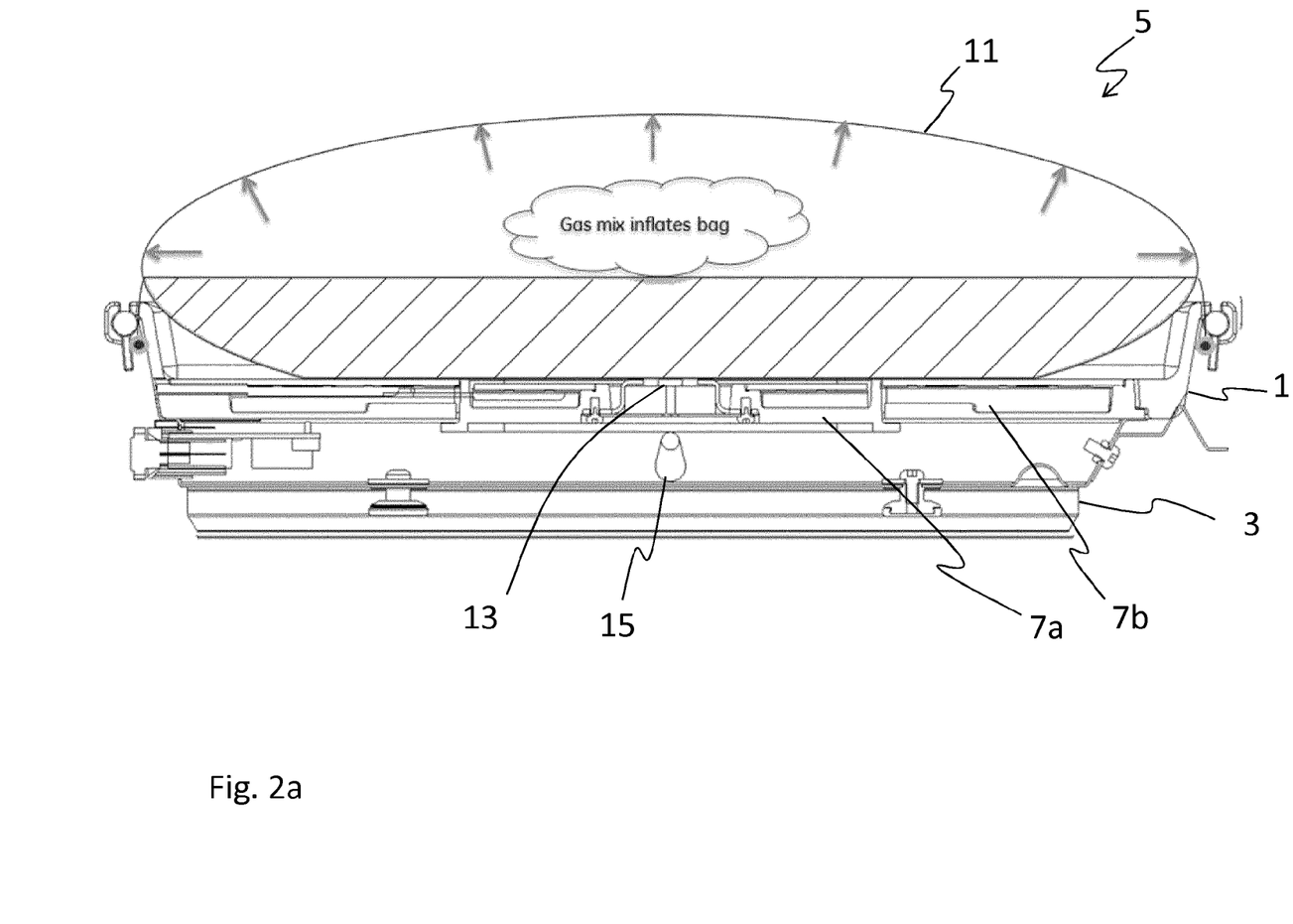
FIG. 2a is a cross section side view of a bioreactor system according to one embodiment of the invention with a first part of the tray bottom provided in a first position.
Figure 2B:
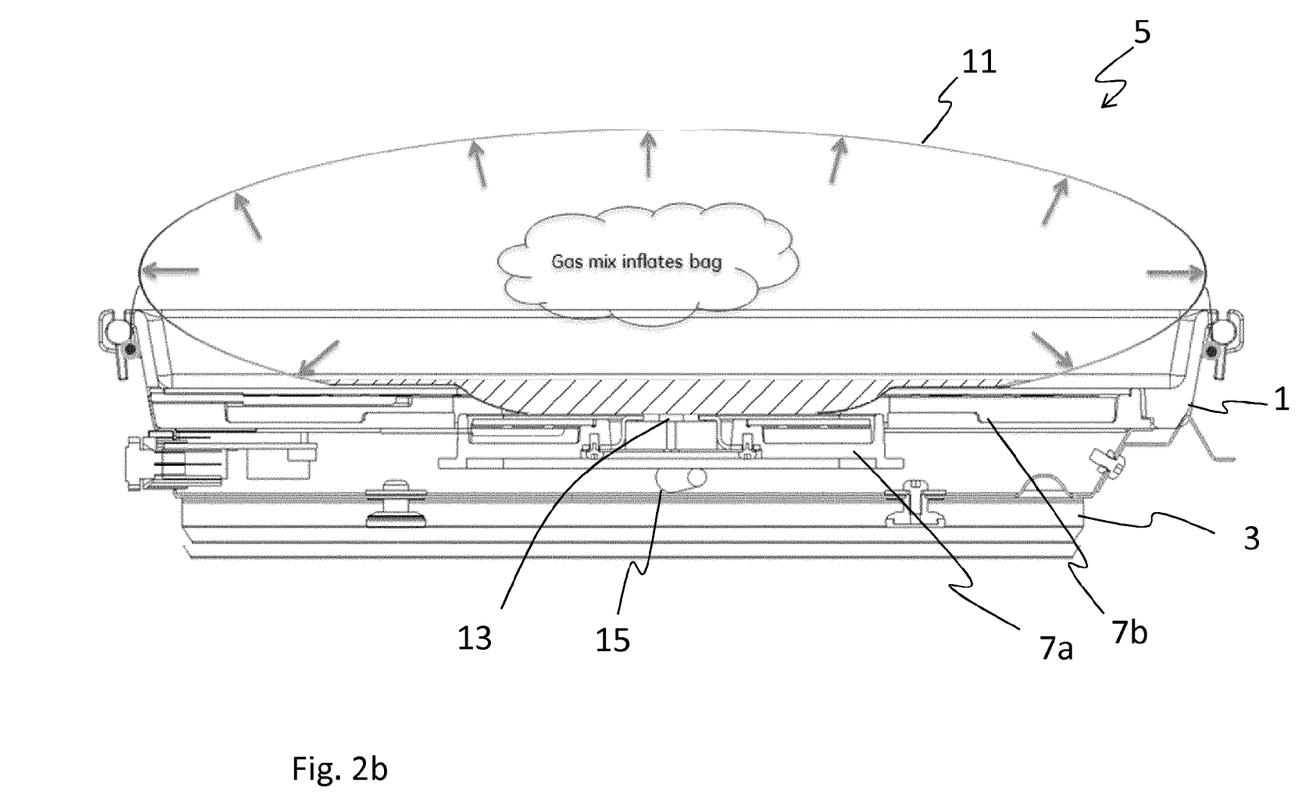
FIG. 2b is a cross section side view of the same bioreactor system as shown in FIG. 2a with a first part of the tray bottom provided in a second position.

FIGS. 2a and 2b show schematically a cross section side view of a bioreactor system according to one embodiment of the invention.

According to the invention a tray 1 which is arranged to be provided on a base station 3 of a rocking bioreactor system 5 is provided. The tray 1 comprises a bottom 7 and surrounding side walls 9 and is arranged to hold a bioreactor bag 11. The bottom 7 comprises at least two bottom parts. In the embodiment shown in FIGS. 1-3 the bottom comprises two bottom parts, a first part 7a and a second part 7b surrounding the first part 7a. In another embodiment of the invention for example three separate bottom parts could be provided. This is shown in FIGS. 4a and 4b. However, common to these embodiments is that one of the bottom parts is a middle part of the bottom. In the embodiment shown in FIGS. 1-3 the first part 7a is a middle part. According to the invention at least one of the bottom parts is movable into at least a first and a second position, wherein said first position provides the bottom parts substantially flush with each other providing a substantially plane bottom 7 of the tray and said second position provides a bottom 7 of the tray having a recessed middle part. In the embodiment shown in FIGS. 1-3 the first part 7a, also called the middle part 7a, is the bottom part which can be moved into at least a first and a second position. In another embodiment it could as well be the one or more other bottom parts, i.e. not the middle part, which is movable into at least two different positions. If one second part 7b surrounding the first part 7a is provided (as in FIGS. 1-3) this second part could be movable into the at least two different positions.

Figure 3:
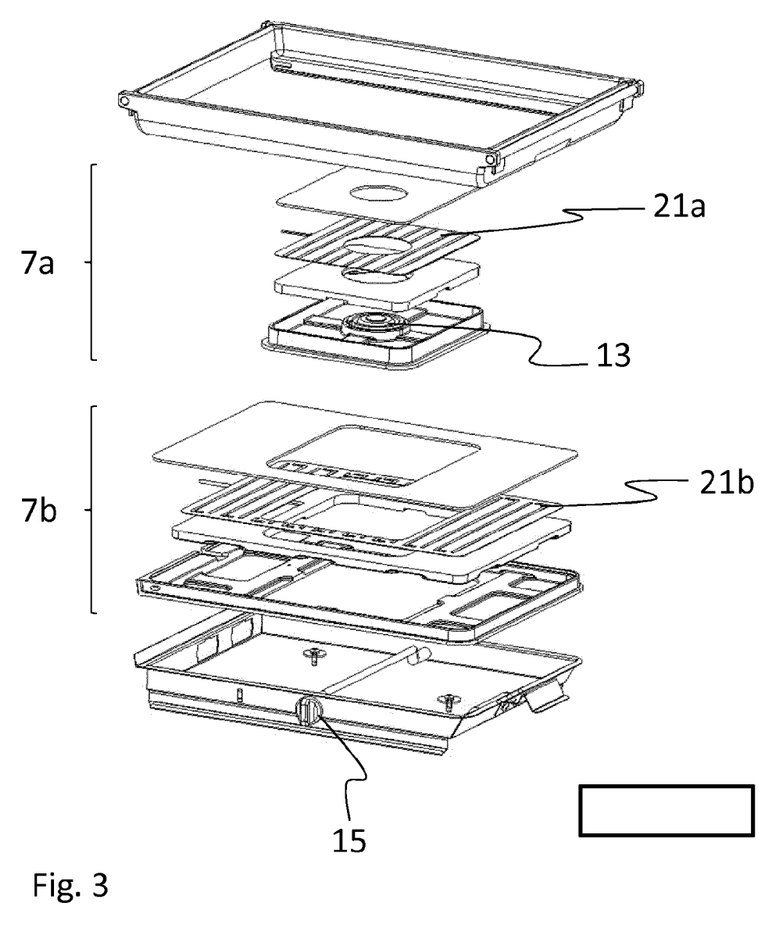
FIG. 3 is an exploded view of a tray according to one embodiment of the invention.
Figure 4A:
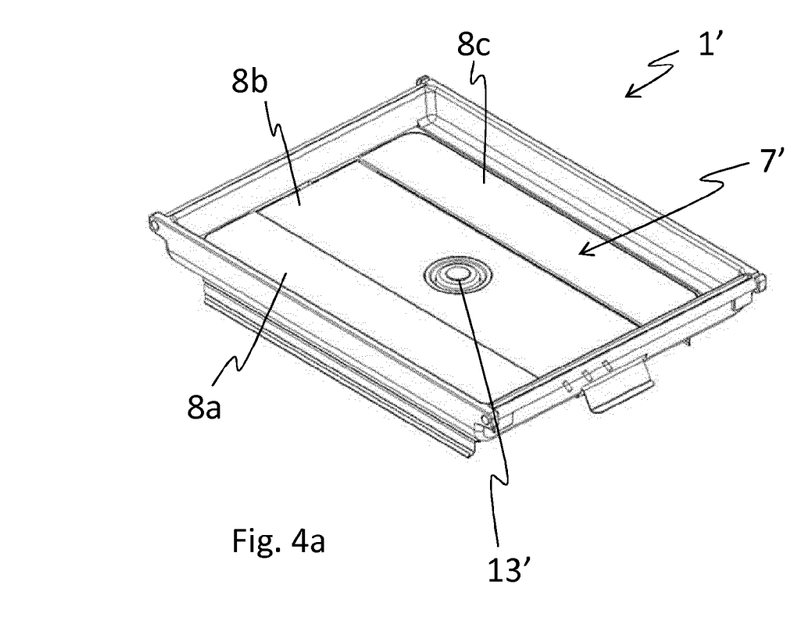
FIG. 4a shows schematically a tray according to one embodiment of the invention.
Figure 4B:
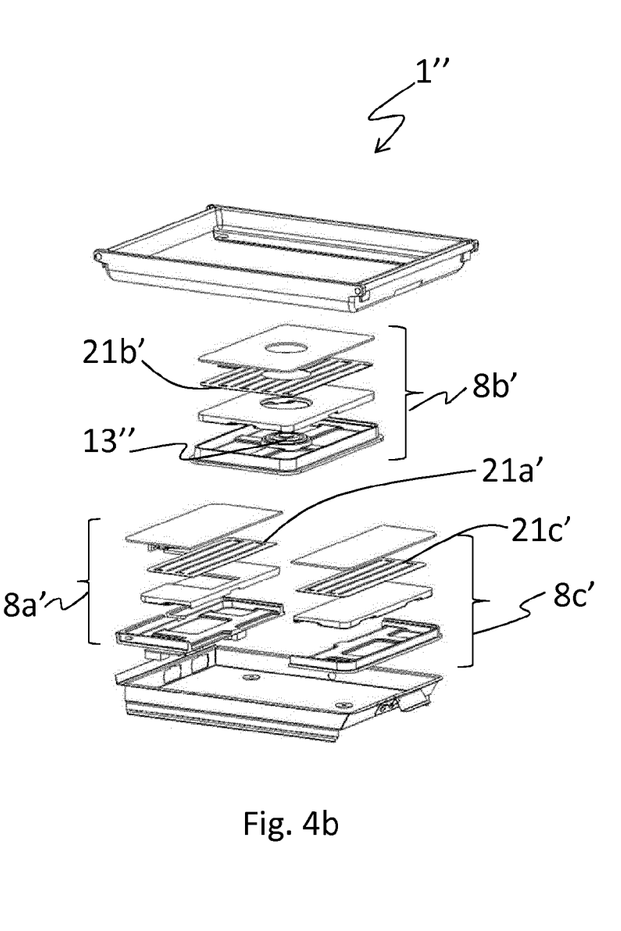
FIG. 4b is an exploded view of a tray according to one embodiment of the invention.

In the embodiment shown in FIGS. 1-3 the first part 7a of the bottom 7 can be provided in two different positions wherein a first position is shown in FIGS. 1a and 2a and provides the first part 7a substantially flush with the second part 7b providing a substantially plane bottom 7 of the tray 1. A second position of the first part 7a is shown in FIGS. 1b and 2b and this is a position where the first part 7a is provided as a recessed middle part of the bottom 7 of the tray. This recessed middle part will house the most of the cell culture volume when the bioreactor bag 11 to be provided in the tray 1 only comprises a small amount of cell culture. Hereby the cell culture will be kept more together within the bioreactor bag during cultivation and during the rocking motion. This is better for the cells and will provide better possibilities for temperature sensing and control of the cell culture. Without this recessed middle part a low volume of cell culture would spread out too much within the bioreactor and be more affected by overheating, condensation and also more damaged by the rocking motion.

In one embodiment of the invention each bottom part comprises at least one heater. In the embodiment shown in FIGS. 1-3, the first part 7a and the second part 7b each comprises one heater. An exploded view of a tray according to one embodiment of the invention is shown in FIG. 3. In the embodiment shown in FIG. 3 a first heater 21a is shown provided to the first part 7a and a second heater 21b is shown provided to the second part 7b. The first and second heaters 21a, 21b are each connected to a control device 31 provided in the base station 3 of the bioreactor system 5. The base station comprising the control device 31 is shown schematically in FIG. 5. The control device 31 can communicate with the first and second heaters 21a, 21b in the tray. This communication could be provided wirelessly or through one or more connection ports 22 between the base station and the tray. By having separate heaters to each bottom part of the bottom of the tray the heating of the bioreactor can be provided in dependence on how much cell culture is provided in the bioreactor bag. Hereby the temperature in the cell culture can be controlled much better also for small volumes of cell culture.

In one embodiment of the invention the middle part of the bottom (the first part 7a in the embodiment shown in FIGS. 1-3) comprises a temperature sensor 13. The temperature sensor 13 is connected to the control device 31 in the base station via a connection port 22 or wirelessly and the control of the first and second heaters 21a, 21b is provided in dependence of the sensed temperature.

The tray 1 comprises further a positioning device 15 by which at least one of the bottom parts can be provided in the at least two different positions. In the embodiment shown in FIG. 1-3 the first part 7a of the bottom 7 can be provided in the at least two different positions. The positioning device 15 is here shown to be an oblong actuation knob which provides the first part 7a of the bottom of the tray in its first position when the knob is provided in a vertical position. In the first position the first and second parts of the bottom are provided substantially flush with each other. The first part 7a of the bottom of the tray is provided in its second position, i.e. lower than the second part 7b, when the knob is provided in a horizontal position. The knob is hereby connected to a transferring means within the tray which can push the first part 7a upwards to its first position. Another type of positioning device 15 can be provided within the scope of this invention. Any device which can move at least one of the bottom parts of the bottom 7 into it's at least two positions should be covered by this invention. For example a motor or solenoid and automatic moving of the at least one bottom part in dependence of for example measured weight of the bioreactor bag is possible.

FIG. 4a shows schematically a tray 1' according to another embodiment of the invention. The tray 1' comprises a bottom 7' and surrounding side walls 9' and is arranged to hold a bioreactor bag. In this embodiment the bottom 7' comprises three separate bottom parts 8a, 8b, 8c. One of the three bottom parts is a middle part 8b and the other two are outer parts 8a and 8c and positioned one on each side of the middle part 8b. Either the middle part 8b or the two outer parts 8a, 8c can be provided in two different positions as described above. A first position provides the bottom parts 8a,b,c substantially flush with each other providing a substantially plane bottom 7' of the tray and a second position provides a bottom 7' of the tray having a recessed middle part 8b. Heaters cannot be seen in this view but can be provided one to each bottom part 8a, 8b, 8c. A temperature sensor 13' can be provided to the middle part 8b. A positioning device (however not seen in this view) is provided to the tray by which at least one of the bottom parts 8a,b,c can be provided in the at least two different positions.

FIG. 4b is an exploded view of a tray 1" according to another embodiment of the invention. Also in this embodiment the tray bottom 7" is separated into three bottom parts 8a', 8b', 8c'. However in the other direction compared to the embodiment shown in FIG. 4a. One of the three bottom parts is a middle part 8b' and the other two are outer parts 8a' and 8c' and positioned one on each side of the middle part 8b'. Either the middle part 8b' or the two outer parts 8a', 8c' can be provided in two different positions as described above. A first position provides the bottom parts 8a',b',c' substantially flush with each other providing a substantially plane bottom 7" of the tray and a second position provides a bottom 7" of the tray having a recessed middle part 8b'. Heaters 21a', 21b', 21c' can be seen in this exploded view one provided to each bottom part 8a', 8b', 8c'. A temperature sensor 13" can be provided to the middle part 8b'. A positioning device (however not seen in this view) is provided to the tray by which at least one of the bottom parts 8a',b',c' can be provided in the at least two different positions.

Figure 5:
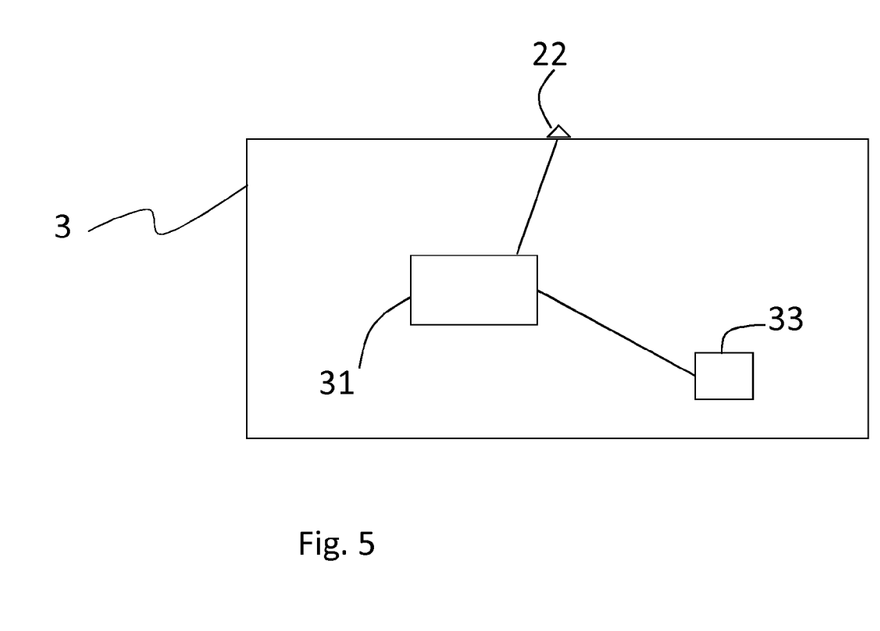
FIG. 5 shows schematically components in a base station of a bioreactor system according to one embodiment of the invention.

In FIG. 5 a base station 3 is schematically shown. A control device 31 is provided in the base station 3. The control device 31 is here shown to be connected to a connection port 22 through which the control device 31 can communicate with the first and second heaters 21a, 21b of the tray. This communication can also be provided through more than one connection port or wirelessly. The control device 31 is configured to control one or more of the heaters provided in the tray in dependence of the position of the at least one movable bottom part of the tray or in dependence of a measured weight of the bioreactor bag. Hereby the control device 31 is further connected to the positioning device 15, 15' in the tray either wirelessly or via a connection port 22 and/or to a weight measuring device 33 provided in the base station 3. If the control device 31 is connected to both a weight measuring device 33 and to the positioning device 15, 15' and the positioning device can be controlled automatically it would be possible to control the position of at least one of the bottom parts of the bottom 7, 7' of the tray 1, 1' automatically in dependence of the weight of the bioreactor bag. The heaters are also controlled in dependence of either the position of one of the bottom parts or in dependence of the weight of the bioreactor bag. Hereby temperature in the cell culture can be controlled with more precision. The control device 31 is also connected to the temperature sensor 13, 13' in the tray which will provide further possibilities for temperature control. The heaters can be controlled in dependence of the sensed temperature.

Figure 6:
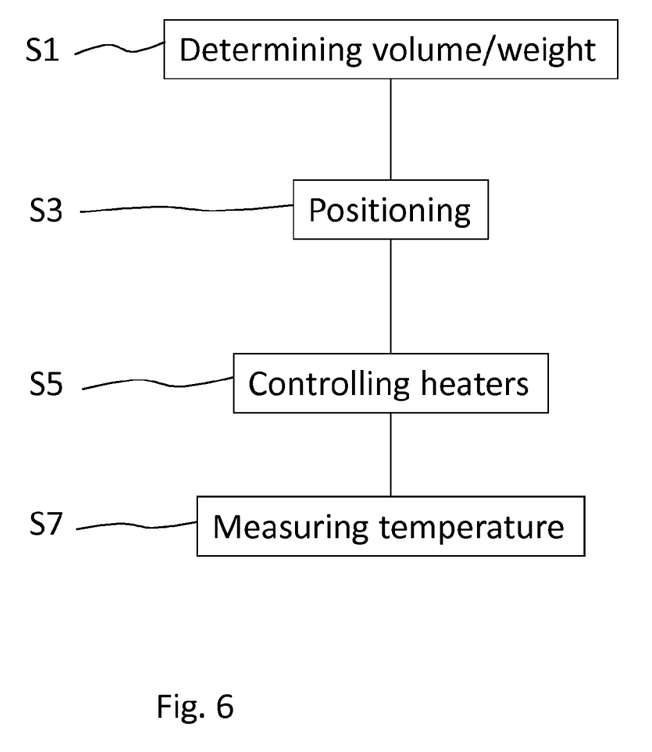
FIG. 6 is a flow chart of a method for culturing cells according to one embodiment of the invention.

FIG. 6 is a flow chart of a method for culturing cells according to one embodiment of the invention. The method steps are described in order below:

S1: Determining a volume or weight of a cell culture provided in a bioreactor bag 11 which is positioned in a tray 1, 1' in the bioreactor system 5. This could be done either manually by the operator making a judgement whether the volume in the bioreactor bag is small or large or automatically by measuring the weight of the bioreactor bag.

S3: Positioning at least one bottom part of a bottom of said tray comprising at least two bottom parts into one of at least a first position and a second position in dependence of said determined volume or weight. Said first position providing the bottom parts substantially flush with each other providing a substantially plane bottom of the tray and said second position providing a bottom of the tray having a recessed middle part. In the embodiment shown in FIGS. 1-3 this step of the method will be to positioning a first part 7a of a bottom 7 of said tray 1 in either a first position or a second position in dependence of said determined volume or weight. This positioning of at least one bottom part of the bottom 7 of the tray 1 can also be done either manually through use of the positioning device 15, for example turning the knob as shown in the embodiment shown in FIGS. 1-3, or automatically in dependence of the measured weight.

S5: Controlling one or more heaters 21a, 21b provided in the tray 1, 1' in dependence of the position of the at least one bottom part which is positioned into at least two different positions or in dependence of a measured weight of the bioreactor bag. A control device 31 in the base station 3 of the bioreactor system 5 is as described above connected to the heaters 21a, 21b and to the positioning device 15 and possibly also to a weight measuring device 33. The control device 31 can hereby turn on the first heater 21a which is provided to the first part 7a of the bottom of the tray when the first part 7a is provided in its second position and the control device 31 can turn on both the first heater 21a and the second heater 21b when the first part 7a is provided in its first position. Hereby a better control of the temperature in the cell culture in the bioreactor bag can be provided.

S7: Measuring a temperature in the bioreactor bag and controlling the heaters in the tray in dependence of said measured temperature. Hereby even better temperature control can be achieved.

The invention claimed is:

1. A tray configured to be provided on a base station of a bioreactor system, said tray comprising:
   a bottom surface and side walls surrounding the bottom surface, wherein said tray is configured to hold a bioreactor bag, said bottom surface comprising at least a middle part and at least one outer part;
   a positioning device, wherein the positioning device is configured to move the middle part into at least a first elevated position and a second recessed position, wherein said first elevated position causes the middle part and the outer part to be substantially flush with each other providing a substantially plane bottom of the tray and said second recessed position causes the middle part to be held in a recessed position relative to the outer part so that the bottom of the tray has a recessed middle part, wherein the recessed middle part is capable of housing a substantial part of a cell culture volume of a bioreactor bag placed on the tray when the bioreactor bag comprises a small amount of cell culture.

2. The tray according to claim 1, configured to be provided on a base station of a rocking bioreactor system.

3. The tray according to claim 1, wherein the middle part and the outer part each comprise at least one heater.

4. The tray according to claim 1, wherein the middle part comprises a temperature sensor.

5. The tray according to claim 1, wherein the tray further comprises at least one heater in each of the middle part and the outer part such that heat may be delivered in dependence of the position of the middle part and the outer part.

6. The tray according to claim 1, wherein the outer part surrounds the middle part.

7. The tray according to claim 1, wherein the positioning device comprises an actuation knob mounted on a central axis and a lever arm extending along the central axis, the lever arm comprising an offset portion that is configured to support the middle part, wherein rotation of the actuation knob causes the offset portion of the lever arm to move upward thereby moving the middle part into the first elevated position, and counter rotation of the actuation knob causes the offset portion of the lever arm to move downward thereby moving the middle part into the second recessed position.

8. The tray according to claim 7, wherein the lever arm extends from the knob on a first side of the tray to the opposite side of the tray.

9. The tray according to claim 7, wherein the knob comprises an oblong portion that is aligned vertically when the middle part is in the first elevated position, and aligned horizontally when the middle part is in the second recessed position.

10. A tray configured to be provided on a base station of a bioreactor system, said tray comprising:
    a bottom surface and side walls surrounding the bottom surface, wherein said tray is configured to hold a bioreactor bag, said bottom surface comprising at least a middle part and a first outer part and second outer part on each side of the middle part;
    a positioning device, wherein the position device is configured to move the middle part into at least a first elevated position and a second recessed position, wherein said first elevated position causes the middle part and the first outer part and second outer part to be substantially flush with each other providing a substantially plane bottom of the tray and said second recessed position causes the middle part to be held in a recessed position relative to the first outer part and second outer part so that the bottom of the tray has a recessed middle part, wherein the recessed middle part is capable of housing a substantial part of a cell culture volume of a bioreactor bag placed on the tray when the bioreactor bag comprises a small amount of cell culture.

11. The tray according to claim 10, configured to be provided on a base station of a rocking bioreactor system.

12. The tray according to claim 10, wherein the middle part and the first outer part and second outer part each comprise at least one heater.

13. The tray according to claim 10, wherein the middle part comprises a temperature sensor.

14. The tray according to claim 10, wherein a temperature sensor is provided in the middle part of the bottom of the tray and wherein a control device is arranged to control the heaters in the tray in dependence of the sensed temperature.

* * * * *